United States Patent
Magri

(10) Patent No.: US 7,022,649 B2
(45) Date of Patent: Apr. 4, 2006

(54) COMPOSITION FOR INOCULATING LEGUMES AND METHOD THEREFOR

(76) Inventor: Juan Bautista Mario Lucio Magri, 2622 Rivadavia, El Bolsón Provincia de Río Negro (AR) 2622 (8430)

( * ) Notice: Subject to any disclaimer, the term of this patent is extended or adjusted under 35 U.S.C. 154(b) by 0 days.

(21) Appl. No.: 10/701,845

(22) Filed: Nov. 5, 2003

(65) Prior Publication Data

US 2004/0092400 A1   May 13, 2004

(30) Foreign Application Priority Data

Nov. 8, 2002   (AR) ............................... P020104287

(51) Int. Cl.
*A01N 63/02*   (2006.01)
*C12N 1/20*   (2006.01)

(52) U.S. Cl. .................... 504/117; 435/252.2

(58) Field of Classification Search ............... 504/117; 435/252.2

See application file for complete search history.

(56) References Cited

U.S. PATENT DOCUMENTS 3,168,796 A * 2/1965 Scott et al. ................... 47/57.6
4,577,468 A * 3/1986 Nunn et al. ................... 62/113
5,586,411 A * 12/1996 Gleddie et al. ............... 47/57.6
5,695,541 A * 12/1997 Kosanke et al. .................. 71/7
5,750,402 A * 5/1998 Guri et al. .................... 435/431

OTHER PUBLICATIONS

Kuykendall et al., "Rhizobium japonicum derivatives differing in nitrogen-fixing efficiency and carbohydrate utilization," Applied and Environmental Microbiology 32(4): 511-519, 1976.*

Bergey's Manual of Determinative Microbiology, 8th Ed., R.E. Buchanan & N.E. Gibbons, eds., pp. 262-264, The Williams & Wilkins Co., Baltimore, 1974.*

ATCC Bacteria and Bacteriophages, 19th Ed., P. Pienta et al, eds., pp. 72 and 301, American Type Culture Collection, Rockville, MD, 1996.*

* cited by examiner

*Primary Examiner*—Robert A. Wax
*Assistant Examiner*—Rosanne Kosson
(74) *Attorney, Agent, or Firm*—Adams Evans P.A.

(57) ABSTRACT

A method for preparing a concentrated inoculating composition which contains a universal use culture medium which is sterilized and cooled, then added to Rhizobium Japonicum and then allowed to multiply for 46 hours. This is followed by the addition to the culture medium of powdered maltose, liquid maltose and lactose saccharides as well as the fungicide potassium sorbate. The general use culture medium can comprise previously treated peat as one of its components. The above results in an inoculating composition for use with leguminous plants with or without peat incorporated as part of the general use culture medium.

2 Claims, No Drawings

COMPOSITION FOR INOCULATING LEGUMES AND METHOD THEREFOR

This application claims priority to Argentinian Patent Application No. P 02 01 04287, Filed Nov. 8, 2002.

TECHNICAL FIELD AND BACKGROUND OF THE INVENTION

The present invention refers to a method for the preparation of a concentrated inoculating composition for legumes, preferably soybeans, alfalfa and beans and the inoculating composition obtained with such a method.

It is known in the art that, under certain conditions, leguminous plants fix nitrogen directly from the air and convert it to certain nitrogenated organic compounds and thus supply nitrogen to the plant for protein synthesis and also enrich the soil, also leaving nitrogenated nutrients for later crops. This fixation is caused by the bacteria named Rhizobium Japonicum or Bradyrhizobium Japonicum existing symbiotically with the plant forming infective nodules in the neck of the root. Nitrogen fixation is a function of the number of infective nodules in the neck of the root, and thus counting the nodules can be used to quantify the efficiency of the inoculant that is used. Therefore, greater nitrogen fixation is achieved with the inoculants containing the highest number of Bradyrhizobium bacteria and, above all, their infectivity.

The inoculants per se were modified in their characteristics from solid substrates such as peat, vermiculite, perlite, charcoal, etc. as carriers of Bradyrhizobium in liquids as the majority of those that are now on the market.

Since the appearance of liquid inoculants, the first problem to solve was to achieve a higher survival rate of the Bradyrhizobium because the period of effectiveness increases as a function of the survival thereof in the inoculant. At an early stage, the viability of one of the inoculants was one month, the majority now lasting as much as eighteen months and some even two years.

The advantage of the liquid inoculants was the greater quantity of bacteria containing $+/-1.00 \times 10^{10}$/ml of Bradyrhizobium and the practicality of their use. On the other hand, they exhibited the disadvantage of greater fragility and hence less viability of their Bradyrhizobium bacteria in the face of attacks by products such as fungicide as well as the dryness of the environment, temperature, pH of the soil, etc.

Solving this problem started with the addition of previously sterilized and neutralized ground peat to the culture medium already prepared with a $1 \times 10^{10}$ concentration of Rhizobium Japonicum, a mixture made prior to the packaging of the culture medium.

Although the addition of the previously sterilized and neutralized ground peat to the culture already prepared with a $1 \times 10^{10}$ concentration of Rhizobium Japonicum improved the viability of the Rhizobium Japonicum bacteria facing the attacks mentioned, which was manifested by improved nodulation, the acidity of the peat itself and its different pH versus the medium in which it was incorporated did not allow an optimum absorption of the Rhizobium Japonicum bacteria. These results were amply overcome by the invention which is submitted for patenting. This invention solves the problem, achieving greater protection, resistance and viability of the Rhizobium Japonicum bacteria facing the attacks previously described and achieving a greater multiplication of the Rhizobium Japonicum bacteria contained in the peat, as will be explained in this specification.

For this purpose, powdered maltose and liquid maltose and lactose saccharides as well as a fungicide called potassium sorbate are added to the culture medium forming the concentrated inoculating composition. The result of all of this is a greater viability of the Rhizobium Japonicum bacteria compared with the viability that the bacteria would have without these additives to the culture medium.

In turn, if peat is simultaneously added with the other ingredients to the general use culture medium, the bacteria will have greater resistance to the attacks mentioned and greater multiplication thereof. This is because of a greater degree of impregnation of the bacteria in the peat incorporating it once the culture medium is finished, there being better neutralization of the acidity of the peat which is combined with the culture medium and takes on the same on the same pH as the latter. It thereby acquires a greater capacity for absorbing bacteria because, at the stabilization temperature, the peat becomes more spongy and thus more porous, thus promoting greater interaction with the bacteria.

SUMMARY OF THE INVENTION

The object of the present invention is a method for preparing a concentrated inoculating composition containing general use culture medium to which is added, after being sterilized and cooled, the Rhizobium Japonicum bacteria which is multiplied at 28° C. for about 46 hours and then allowing the culture medium to which it is added to cool until the latter reaches a temperature of 10 to 11° C., the method being characterized in that, once the steps mentioned have been completed, powdered maltose and liquid maltose and lactose saccharides as well as a fungicide called potassium sorbate are added to the culture medium. The result of all of the above is a concentrated inoculating composition useful in industrial and agricultural terms for employment with leguminous plants, preferably soybeans, alfalfa and beans.

Another object of the present invention is a method for preparing a concentrated inoculating composition containing general use culture medium to which is added, after sterilized and cooled, the Rhizobium Japonicum bacteria which is multiplied at 20° C. for about 46 hours and then allowing the culture medium to which it is added to cool until the latter reaches a temperature of 10 to 110° C., the method being characterized in that, during preparation of the general use culture medium, treated peat is added as one of its components and, after completion of the steps described, powdered maltose and liquid maltose and lactose saccharides as well as a fungicide called potassium sorbate are added to the inoculant. The result of all of the above is a concentrated inoculating composition with peat incorporated initially as one more component of the culture medium containing the inoculant useful in industrial and agricultural terms for employment with leguminous plants, preferably soybeans, alfalfa and beans.

Another object of this invention is a concentrated inoculating composition prepared in accordance with one of the two methods just described.

Other objects, advantages and features of the present invention will become more evident in the following detailed description, the example embodiments not being limiting and given only to illustrate the invention.

The invention describes an industrial method for preparation of a concentrated inoculating substance with or without peat incorporated as part of the culture medium, agriculturally useful, practical and efficient, above all when mixed with fungicides and the resulting inoculant.

The culture medium to which we refer throughout the specification is a general use culture medium, each 1000 liters of which contains preferably 500 g of potassium phosphate, 300 g of ammonium phosphate, 200 g of magnesium sulfate heptahydrate, 800 g of potassium nitrate, 100 g of sodium chloride, 12.5 kg of glycerine, 4 kg of yeast extract, 100 ml of 10% ferric chloride and 200 ml of anti-foaming agent.

One preferred way of applying the invention consists in a method for preparation of a concentrated inoculating composition, the general use culture medium of which is sterilized and cooled and then injected with the Rhizobium Japonicum bacteria. In this culture medium, the bacteria is multiplied for approximately 46 hours at a temperature of 28° C. The culture medium with the bacteria already incorporated is then cooled to a temperature of 10 or 11° C. Once these steps are carried out, 500 g of maltose saccharide, 2.5 kg of liquid maltose saccharide and 500 g of lactose saccharide are added to the culture medium. Also added are 400 g of a fungicide called potassium sorbate. In order to add all these last components to the culture medium, they must be dissolved in 100 liters of water and then sterilized at 121° C. for 30 minutes, allowing the mixture to cool until it reaches a temperature of 20° C. and then transferring these components to a tank containing the universally known culture medium. The result of adding these components treated in the way described to the culture medium is a concentrated inoculating composition, agriculturally useful, practical and efficient, especially when mixed with fungicides.

Another way of embodying the invention consists in adding 100 kg of previously treated peat to the general use culture medium as one of its components, this addition being carried out simultaneously with the other chemicals forming a part of the general use culture medium described herein. For this purpose, the peat requires previous treatment which consists in heating the peat with distilled water to 100° C. for forty minutes in order to evaporate the different volatile components of the natural composition of the peat. After this, 10% of the final volume of the peat is transferred to the fermenting unit for preparation of the culture medium to which is added the remainder of the previously mentioned chemicals, adjusting the pH in accordance with the usual standards of the process for fermenting Rhizobium. 500 g of maltose saccharide, 2.5 kg of liquid maltose saccharide and 500 g of lactose saccharide are added to the culture medium. Also added are 400 g of a fungicide called potassium sorbate. In order to add all these last components to the culture medium, they must be dissolved in 100 liters of water and then sterilized at 121° C. for 30 minutes, allowing the mixture to cool until it reaches a temperature of 20° C. and then transferring these components to a tank containing the universally known culture medium. The result of adding these components treated in the way described to the culture medium is a concentrated inoculating composition, agriculturally useful, practical and efficient, especially when mixed with fungicides.

The previously treated peat must preferably comprise 5 to 20% by weight of the culture medium.

The previously treated peat must preferably comprise 5 to 20% by weight of the culture medium.

The following analyses carried out in laboratories will illustrate the benefits of the invention compared with the previous art.

The bacteria is added to the general use culture medium and an assessment is then made of its viability which should reach a life of 40 days. After this, 500 g of maltose saccharide, 2.5 kg of liquid maltose saccharide and 500 g of lactose saccharide are added to the culture medium. Also added are 400 g of a fungicide called potassium sorbate which achieves a viability of 18 months. The liquid maltose as well as the powdered maltose can be replaced by trehalose.

Another test is carried out by mixing the inoculant with 10 to 20% peat with seed-treating agents Tiram and Carbendazin (30/30). It is left standing for eight hours and viable count (V.C.) is carried out. This is then mixed with seeds in a proportion of 0.4 g per 100 g of seed. Sowing is then carried out in the laboratory in a way that is universally known (in accordance with the method proposed by the S.E.N.S.A.). At the end of 21 days, a count is made of the nodulation with the results given in Table I below:

|  | V.C., initial | V.C., 8 h | Nodulation |
| --- | --- | --- | --- |
| Sample A: Liquid inoculant without peat + seed-treating agent | $5 \times 10^9$ | $4 \times 10^8$ | 4 nodules per plant |
| Sample B: Liquid inoculant with peat + seed-treating agent | $5 \times 10^9$ | $2 \times 10^9$ | 10 nodules per plant |

Tests were also carried out with soybean seed with the proportion given in accordance with the use of liquid inoculant+seed-treating agent and liquid inoculant with peat in the composition+seed-treating agent.

The seeds were left for eight hours in the culture oven at a temperature of 38° to 40° C. followed by a V.C. in the seeds and the nodulation to determine the survival of the bacteria, as is illustrated in the following Table II:

|  | Initial | 8 hours | Nodulation |
| --- | --- | --- | --- |
| Sample A | 150,000 bacteria per seed | 50,000 bacteria per seed | 2 nodules per plant |
| Sample B | 150,000 bacteria per seed | 90,000 bacteria per seed | 6 nodules per plant |

The two preceding tables are the average of more than fifty analyses carried out. The prior art does not include a method of preparation of the product described nor this one either, being unique in that it has peat incorporated in the culture medium as a component thereof.

Another method is carried out by centrifuging the inoculant to separate the solid (peat) from the liquid culture medium, rinsing with distilled and sterile water, discarding the wash water. After this, 10 g of the peat are taken and subjected to a viable count and a nodulation count with the results in Table III below:

|  | V.C | Nodulation |
| --- | --- | --- |
| Peat incorporated in the finished culture medium | $1 \times 10^9$ | 5 nodules per plant |
| Peat incorporated in the culture medium simultaneously with the other components thereof | $9 \times 10^9$ | 12 nodules per plant |

These figures are the average from more than fifty tests carried out.

I claim:

1. A method for preparing a concentrated inoculating composition for use with leguminous plants, comprising me following steps in the order given:
   a) sterilize and cool a culture medium suitable for supporting the growth of Rhizobium japonicum bacteria;
   b) add Rhizobium japonicum bacteria to the culture medium and allow to multiply for 46 hours at a temperature of 28 C.;
   c) cool the result of step b) to a temperature of 10° C. or 11° C.;
   d) add a solution comprising powdered maltose saccharide, liquid maltose saccharide, lactose saccharide, and potassium sorbate to the combined culture medium and bacteria, said solution being prepared by the following steps:
   1) dissolving said powdered maltose saccharide, said liquid maltose saccharide, and said potassium sorbate in 100 liters of water;
   2) steriling at 121° C. for 30 minutes;
   3) cooling to 20° C.

2. The method for preparing a concentrated inoculating composition as described in claim 1, further comprising the step of incorporating, prior to step a), a suspension of peat that makes up 5 to 20% by weight of the inoculating composition and which has been treated in accordance with the following steps:
   I) heat the peat with distilled water at 100° C. for forty minutes;
   II) transfer 10% of the final volume of the peat of step I to a fermenting unit where the culture medium is to be prepared and where are added the rest of the chemicals which comprise the culture medium;
   III) adjust the pH to between about 6.9 to about 7.0.

* * * * *